United States Patent [19]

Stage

[11] Patent Number: 4,680,092

[45] Date of Patent: Jul. 14, 1987

[54] PROCESS FOR DEGASSING, DEHYDRATING AND PRECUT SEPARATION IN STRAIGHT-RUN DISTILLATION OF CRUDE FATTY ACIDS

[76] Inventor: Hermann Stage, Ludgeristrasse 9, 4400 Muenster, Fed. Rep. of Germany

[21] Appl. No.: 539,288

[22] Filed: Oct. 5, 1983

[30] Foreign Application Priority Data

Oct. 6, 1982 [DE] Fed. Rep. of Germany ....... 3236985

[51] Int. Cl.$^4$ ............................ B01D 3/38; C11C 1/10
[52] U.S. Cl. ...................................... 203/22; 203/72;
    203/78; 203/79; 203/80; 203/87; 203/93;
    55/54; 55/55; 202/159; 202/179; 202/186;
    202/198; 260/419
[58] Field of Search ...................... 203/92-97,
    203/88, 79, 80, 78, 87, 85, 71, 22, DIG. 14, 39,
    14, 4; 202/176, 180, 177, 186, 234, 205, 179,
    198, 159, 236; 260/428, 419; 55/54, 55;
    196/139; 210/750, 188

[56] References Cited

U.S. PATENT DOCUMENTS

| | | | |
|---|---|---|---|
| 926,216 | 6/1909 | Slavicek | 202/159 |
| 1,034,267 | 7/1912 | Mattingly et al. | 202/179 |
| 2,071,693 | 2/1937 | Hines | 202/159 |
| 2,447,746 | 8/1948 | Ferris et al. | 159/49 |
| 2,674,570 | 4/1954 | Potts | 203/92 |
| 2,722,505 | 11/1955 | Faulkner | 203/92 |
| 2,938,838 | 5/1960 | Ballestra | 202/176 |
| 3,197,386 | 7/1965 | Lau | 203/92 |
| 3,607,670 | 9/1971 | King | 203/92 |
| 4,089,880 | 5/1978 | Sullivan | 260/419 |
| 4,394,221 | 7/1983 | Stage et al. | 159/3.2 |

FOREIGN PATENT DOCUMENTS 2352859 4/1975 Fed. Rep. of Germany.
2736357 2/1979 Fed. Rep. of Germany.

Primary Examiner—Wilbur Bascomb
Attorney, Agent, or Firm—Watson, Cole, Grindle & Watson

[57] ABSTRACT

The invention concerns a process for the degassing, dehydrating and lower boiling component separation during straight-run distillation of crude fatty acids. The crude fatty acids are degassed in the degassing stage at such temperatures and pressures in counter current flow with stripping steam that no appreciable dehydration or lower boiling component separation takes place at this stage, then the degassed crude fatty acid is then led to a precut column for dehydration and lower boiling component separation, whereby the falling film concentrator column operates as a partial condensation stage for the creation of the reflux of the fatty acids, which is necessary for the lower boiling component separation, and that the easily boiling component evaporates almost completely in the precut column and is led off from the precut column in vapor form, together with the water.

8 Claims, 1 Drawing Figure

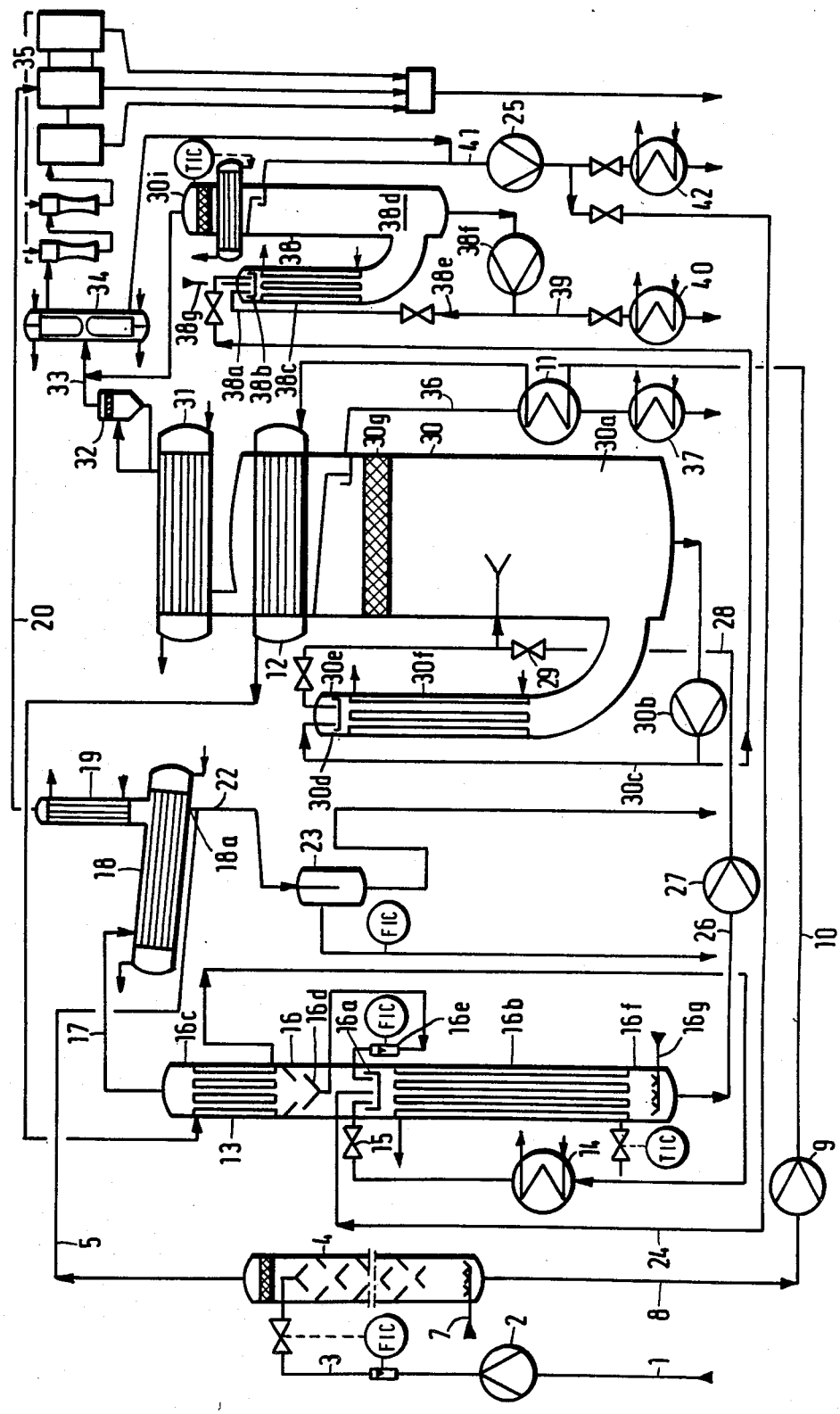

PROCESS FOR DEGASSING, DEHYDRATING AND PRECUT SEPARATION IN STRAIGHT-RUN DISTILLATION OF CRUDE FATTY ACIDS

BACKGROUND OF THE INVENTION

1. Field of the Invention

This invention relates to a method of distilling crude fatty acids, and more particularly to a method of degassing, dehydrating and preliminarily purifying the crude fatty acids prior to being distilled, as well as to an apparatus for accomplishing such a method.

2. The Prior Art

It has been known for a long time that, in the straight-run distillation of fatty acids, the quality of the fatty acids obtained from the main distillation stage can be improved, i.e., the amount of undesirable components therein such as carbohydroxides, aldehydes, ketones and peroxides reduced, if these precut (lower boiling) components are separated out of the crude fatty acid in a preliminary step prior to reaching the main distillation stage. Such separations have been conducted in the past at the same time as the conventional dehydrating and degassing steps which have almost always been accomplished under the same or nearly the same pressure conditions as are found in the main distillation stage, i.e., at 2.66 and 40 mbar. However, these known processing procedures have the disadvantage that the lower boiling (precut) components are only partially separated from the crude fatty acids.

The lower boiling components result from oxidative and/or thermal conditions to which the crude fatty acids are subjected prior to and during the distillation thereof, such as during oil and fat removal steps, cleaning, storage and separation steps. During these procedures, the oxidative and thermally sensitive acid components, which are more or less unsaturated, are exposed to high thermal and/or oxidative conditions even when the treatment apparatus is well sealed, and small amounts of cleavage products result. This is especially true with crude fatty acids which are very unsaturated, i.e., they have more than one double bond in the molecule, and specifically when the acids are subjected to high temperatures in the distillation apparatus. These cleavage products undesirably appear in the main condensate in prior art processing systems.

When using a partial condensation apparatus for the main production, an apparatus normally used when there is a need for using generally larger amounts of carrier steam to achieve the distillation separation from the high-boiling matter, the lower boiling components appear mainly in the radiation drain water. Although this process provides an improvement in the main production distillate quality without, however, making it possible to get total separation, the process has the disadvantages of an especially high energy demand for the condensation of the carrier steam used and a considerably larger output of drain water which is loaded with organic matter. This should be absolutely avoided, considering todays sewage output in the whole world and treatment of the drain water to eliminate the organic matter contained therein is very expensive.

According to a more recent procedure developed by the present inventor (see German Pat. No. 2352859), the separation of these components is done by means of rectification with a column which has both an effective concentration portion and a stripper portion. The stripper portion is constructed as a trickle film column in the shape of a counter current film evaporator and the concentration portion is constructed as a floor or fill column. The fill column is operated with top pressure of between 67 and 400 mbar and with a bottom temperatures in the range of 170°–210° C., so that the water contained in the crude acid, which evaporates at the working temperatures employed, condenses together with the only slightly water-soluble organic lower boiling components using cooling water in the temperature range of between 38° and 80°. The condensate is then divided into an upper lighter organic phase and a lower heavier water phase during the subsequent phase divider step and only the organic phase is fed to the head of the concentrator column in a return flow.

An object of the present invention is to achieve a more thorough and reliable separation of the precut or forerunnings (lower boiling components) as compared to the above procedure. Another object of the invention is to provide a treatment process in which the energy requirements are considerably reduced and in which the degree of pollution of the waste water is also reduced.

According to the invention, and unlike the processes in German Pat. No. 2352859, the separated precut components will not enter into the precut column, but rather forms the return flow in the concentrator part of the main distillation apparatus which is constructed as a fractionating condenser.

SUMMARY OF THE INVENTION

The present invention is for the degassing, dehydrating and precut separation during straight-run distillation of crude fatty acids, wherein super heated stripping steam is fed in a lead column in counter current flow to the crude fatty acid to be treated wherein the stripping steam which is fed through a column stripper for the crude acid, is fed through the distributor or near the distributor of the stripping column, into a enriching column, which operates on the distributor of the stripping column that is covered by the crude acid, and whereby the column vapors which reach the head of the column are condensed, characterized by the facts that the crude fatty acids are degassed during a degasification stage at such temperatures and pressures with counter current flow of the stripping steam, that there is no appreciable dehydration or precut separation in the degassification stage, that the degassed crude fatty acid is then led to a precut column for dehydration and precut separation, whereby the falling film concentrating column operates as a partial condensation stage for the generation of the reflux of the fatty acids necessary for the precut separation, that the easily boiling precut in the precut column just about completely evaporates and is condensed as steam from the precut column together with the water, and that in an actually known manner, water and precut condensate are collected in a decantation tank and are drawn off from the tank, preferably separately.

Because of the type of precut separation conducted in the invention, there is a very distinct difference in concentration between the return flow created by the fractionating effect and the organic distillate product because of the large gap in boiling points between the precut components and the fatty acids which can be effectively utilized in this manner. Added to this is the considerably shorter dwell time for the precut components which accumulate in the rising steam mixture, which are, at the exit temperature at the tip of the factionating column (which is, e.g., 178° C. for R=8 at 200 mbar), still in the form of vapor with the corresponding amount of carrier steam.

An essential requirement for the thermal stability of the acids is also the complete absence of oxygen which can react immediately with the fatty acids at higher temperatures, particularly those acids with double bonds. It was discovered that it is possible to effectively avoid such an oxidation reaction by degassing the crude acid at the temperature range of the crude acid supply tank of <100° C., preferably <70° C., with a moderate working pressure of 67–400 mbar, and preferably 133–267 mbar, in a counter current stripper column while using 0.1–0.4% by weight, and preferably 0.15–0.3%, of absolutely air-free pure carrier steam is an exchange medium as opposed to air and other inert gas parts. During degassing, the pure carrier steam is introduced into the bottom of the degassing stage and travels upwardly in a counter current direction to the downwardly falling liquid film, which always renews the surface. The resulting temperature increase of 1.4°–2.8° C. in the acid does not result in an appreciable dehydration of the supplied crude acid at the above stated operating conditions of pressure and temperature. Dehydration only takes place in the subsequent dehydration and percut stage, which is operated, as is the degassing stage, at pressures between 67 and 400 mbar, preferably between 133–267 mbar.

The completely gas free supply product which is drawn off from the degassing stage can now be heated up in a continuous operation without danger. The acid may be heated up to a supply temperature of about 180° C.–200° C., depending on the working pressure used during the main stage of between 1.33 and 13.32 mbar, or rather preferably 2.6–7.98 mbar. Heating of the acid is accomplished initially by heat exchange with the sensible heat of the distillate of the main stage, which, e.g., cools at 2.66 mbar top pressure from 188° C. to 102° C. by itself and causes a heating of the supply acid up to 140° C. For heating the acid up to about 175° C., a portion of the condensation heat of the main stage is used. To heat the acid further to a temperature greater than 180° C., the heat in the falling film dephlegmator of the preliminary step is available where the non-condensed fraction of the steam, together with the water vapor, cools down to about 178° C. For a top pressure of 200 mbar, this temperature corresponds to the one of the steams leaving the head of the falling film dephlegmator, relative to the organic component of the steam mixture which enters the dephlegmator at the bottom, a reflux ratio of R=8. Thus 8 parts of the organic component of the rising steam are condensed, while a portion is fed, together with the non-condensed carrier steam, to the final condenser with the final gas cooling component. If the temperature of the cooling water is 40° C. upon entry into the gas cooler at the exit point of the gas, it is possible to maintain a gas exit temperature of 45° C. This corresponds to a water content in kg/h for the released inert gas of less than ⅔ of the released inert gas in kg/h, both of which have to be suctioned off hourly by a vacuum installation. The content of fatty acid resulting from the corresponding fatty acid partial pressure for the stated waste gas temperature of 45° C. is <0.001% by weight of the released amount of waste gas saturated by water vapors. For an installation which processes 6.5 tons crude acid per hour, this is, e.g. <0.00005 kg/h, released hourly into the radiation water and dissolved by it. Added to the waste is the water produced in the preliminary step as a lower phase of the distillate divider, which is also fed into the waste water stream from the drop water box of the vacuum installation, to be subsequently cooled down to about 25° C., together with the latter for the further expulsion of organic matter. The resultant lower watery phase is used as circulating cooling water for the vacuum installation, from which, in each case after the last decantation tank, for a dwell time of at least 2 hours, the genuine waste water supply of the preliminary step and of the hourly radiation steam use, including the strip steam added in the final phase and the water content of about 0.05% of the through flowing amount remaining from the drain of the preliminary step, is drawn off at 25° C.

DESCRIPTION OF THE DRAWING

The accompanying drawing schematically depicts an apparatus which can be used in distilling a crude fatty acid stream according to the present invention.

DETAILED DESCRIPTION

The process of the invention will be better understood by reference to an example procedure wherein crude soy acid is distilled in an apparatus as is schematically depicted in the attached drawing. The crude soy acid had the following composition:

| | | |
|---|---|---|
| $H_2O$ | 130.0 kg/h | 130.0 kg/h |
| $C_{14}$-FS | 6.4 kg/h | |
| $C_{16}$-FS | 505.2 kg/h | |
| $C_{16'}$-FS | 4.0 kg/h | |
| $C_{18}$-FS | 286.2 kg/h | |
| $C_{18'}$-FS | 1526.4 kg/h | 6356.7 kg/h |
| $C_{18''}$-FS | 3372.6 kg/h | |
| $C_{18'''}$-FS | 487.8 kg/h | |
| $C_{20}$-FS | 38.1 kg/h | |
| $C_{20'}$-FS | 127.0 kg/h | |
| Oil | 250.0 kg/h | 250.0 kg/h |
| | 6736.7 kg/h | 6736.7 kg/h |

6682.4 kg of the crude soy acid with an entry temperature of about 60° C. is fed via pipe 1, supply pump 2 and pressure pipe 3 into the stripper 4 at a point above the stripper elements therein, the stripper 4 functioning as a degassification stage. A vacuum pipe 5 connects the top of the stripper 4 to a main condenser 18, operating as a subsequent preliminary stage for aeration and evacuation at a top pressure of 200 mbar. Pure stripping steam is supplied to the bottom of the stripper 4 via a line 7, the stripping steam acting to degas the crude soy acid. The steam flows at a volume of 5–30 kg/h, preferably 10–20 kg/h. The temperature of the crude acid is caused to rise by 1.5° to 3.0° C. in the stripper 4.

From the bottom of the degassing stage the degassed crude acid inflow is first led through the suction pipe 8, transport pump 9 and then pressure pipe 10 for heat exchange in the main distillate cooler 11, where the inflow is heated from 60° C. to 140° C. and the distillate is cooled from 188° C. to 102° C. Then the in flow is fed into the to heat exchange condenser 12 of the main stage where it is heated to about 175° C., and then is fed on to the falling film dephlegmator column 13 of the preliminary and dehydration stage where it is heated to 180° C. The remaining heating of the crude acid in flow to the inflow temperature of 225° C. takes place in the heat exchanger 14 which is heated by a high temperature heating medium, whereby the median temperature difference for the entry temperature of the heating medium of 250° C. is 27.4° C. For an exchange surface of 60 m² there is a heat transfer number k of 137.2 kcal/m²·°C·h.

Above preliminary precut above the liquid distributor 16a for the stripping column in the form of falling film evaporator 16b, there is located the supply line from a pressure-release valve 15, which is relieved by a pressure of 210 mbar in the inflow, whereby, together with 125 kg water, some 161 kg fatty acid and components with low boiling points evaporate spontaneously. The vapors developed there enter, together with those developed by the falling film evaporator 16b, in the enriching column in the form of falling film dephlegmator column which is installed vertically above it. The return flow condensate, which precipitates on the inside walls of the cooling pipes, moves in counter current flow to the rising vapors and exchanges itself with them. With a pipe length of 2 m and 38 mm inside diameter, this counter current enriching column has an exchange effect of more than two theoretical exchange units. The vapors are at 178° C. when then leave the enriching column 13 an enter the head 16c where the pass through a pipe 17 to the final condenser 18 having 45 m² exchange surface. The vapors then pass to the gas cooler 19 with 5 m² exchange surface, from which the inert gases at 45° C. are led to the vacuum connection pipe 20. At the exit from the gas cooler, the gases have a pressure is 200 mbar. Under these conditions, the vacuum installation is charged, in addition to the inert gas, with air at 3 kg/h from the degassing stripper 4 and the preliminary precut column 16 and corresponding partial water steam pressure at <2 kg/h water vapor. Connection of the degassing stripper 4 occurs at the corresponding enlarged condensate exit joint 18a of the condenser 18, so that the waste gas from degassing stripper 4, which arrives at 63° C., is cooled in the condenser 18 and gas cooler 19 together with the waste gas of the preliminary stage to the noted exit temperature of 45° C. The water content of the exiting gas corresponds to this temperature. The liquid condensate of water and organic particles which are only slightly soluble in each other, as produced by the condenser 18, is led through a pipe 22 to the divider 23, where division into an upper organic phase of 25 kg hourly and a lower watery phase of about 177 kg/h takes place.

50 kg of the watery phase result from the amount of pure stripping steam which is added to the bottom 16f of the falling film evaporator 16b through line 16g. The watery phase which occurs here continuously and which is saturated with organic particles at about 50°-55° C., is combined with the radiation waste water for further elimination of organic particles and cooled—in a circulatory system which is not shown here—to about 25° C. During a dwell time of more than two hours, additional organic particles collect on the surface where they have to be skimmed off from time to time, so that an admissible content of organic particles is reached in the subsequent cooling water circulation steam for the waste water from the injection cooler of the vacuum installation.

The condensate which exits from the bottom of the enriching column 13 of the preliminary stage is collected by a collection device 16d with sufficient available diameter and is, as already mentioned, fed together with the liquid phase of the inflow stream to the pressure release valve 15 and the liquid distributor 16a.

In the falling film evaporator 16b, the stripping of the remaining water and precut (lower boiling) parts takes place with the addition of pure steam in a corresponding amount to the bottom 16f, using the distribution installation 16g. With a pipe length of 8 m, there are 6-8 theoretical exchange units available for the stripping procedure.

In addition to the 6736.7 kg of crude acid inflow, the 165 kg/h of distillate phase obtained from the pitch stage are added, if needed, to the preliminary precut column 16 for supply to the distribution floor 16a, the distillate being added through the pressure pipe 24 of pump 25, in order to get the latter also by double distillation in the main stage as main distillate.

With heat added to the falling film evaporator 16b, the fatty acid is heated to the acceptable outflow temperature of 235° C. for soy fatty acid. The falling film evaporator 16b consists of 50 pipes with an outer diameter of 57 mm and an inner diameter of 53 mm with a length of 8 m. The exchange surface available for the counter exchange is 71.63 m². For the inside circumference of 8.33 m, there is a liquid charge of 1.07 m³/m·h. For the amount of carrier steam added to the bottom 16f through the distributor 16g, including the fatty acid part of about 80 kg/h which is carried along by the steam, there is at the head of the evaporation pipes for the existing pressure a comparable air speed of $V_L = 3.39$ m/sec., a speed which is within the acceptable range for the existing counter current flow of the rising steam and the liquid film running down the pipe wall.

Through the suction pipe 26, the pump 27 and the pressure pipe 28 with the pressure release valve 29, the crude acid which has been freed of the lower boiling components is fed into the divider 30a of the main evaporation stage 30, which is maintained at 4 mbar. Some 1900 kg of fatty acid evaporate spontaneously by the pressure release. The 4792.4 kg which remain liquid in the liquid phase mix in the well of divider 30a with the liquid part of the circulation steam from the corresponding main drop film evaporator, which amounts to about 180 m³/h, from which 460 kg/h are branched off as inflow for the subsequent pitch stage. The circulation takes place with the hermetic pump 30b through suction and pressure pipe 30c to the liquid distributor 30e, located in the evaporator head 30d, which gives assurance that the condensation of liquid is even throughout the circumference and length of the pipe walls of all 360 evaporator pipes of the pipe bundle 30f. Each evaporator pipe has 76 mm outside diameter, 72 mm inside diameter and a length of 1000 mm. For the available exchange surface of 86.0 m², the pressure is only 0.133 mbar, which is <5% of the pressure of 4 mbar in the corresponding divider room 30a for, on the one hand, the transfer of 1779 390 kJ at a median temperature difference of 20° C. between the high temperature heating medium and the evaporated fatty acid film with the heat transfer number 247.1 kcal/m²·°C·h and, on the other hand, the pressure loss which the vapors developed in the drop film evaporator have to overcome. The liquid change per m pipe circumference at the upper and lower end of the evaporator pipes are 2.20 and 2.12 m³/m·h respectively, so that a contiguous film of liquid is guaranteed over the length and circumference.

The comparable air speed in the dividing room 30a, because of the pressure release of the inflow and the evaporation of the drop film evaporator, is, with the chosen diameter of 4.2 m, 0.700 m/s below the Euroform liquid drop divider 30g at 4 mbar and 7.48 m/s below 30g for the pressure of 3.33 mbar.

In the heat exchanger 12 installed above drop divider 30q, 565218 kJ condensation heat is removed from the vapors and is used for preheating the inflow from 140° C. to >175° C. The exchange surface of 30 m² available corresponds to a heat transfer number of k=180.1 kcal/m²·°C.·h. Since a total of 2524640 kJ/h have to be led off from the condensation zone, the final condenser 31, installed above the heat exchanger 12 and provided with cooling water of 40° C., has 30 m² of exchange surface arranged such that even during shut down, when no more heat is taken from the heat exchange condenser 12 after the inflow has been shut off, the final condenser can take up the stated total condensation heat. With the cooling water entry and exit temperatures of 40° C. and 55° C., the heat transfer number is 165.6 for the full output without preheating of the product in exchanger 12 under the conditions stated.

A suitably sized Euroform drop divider 32 is in the waste gas pipe directly above the final condenser 31 for separating out the smallest drops of liquid that have been carried along from the waste gas stream coming out of the condenser at a flow of 3 kg/h water vapor from the inflow stream and at <2 kg/h dead air. The waste gas then enters the vacuum pipe 33 which leads through the gilled pipe cooling trap 34 to the five-stage vacuum steam radiation installation 35 at a suction pressure of 1.33 mbar. The corresponding vacuum pipe of the final stage for the pitch separation, working at the same head pressure as the main stage, also joins into this pipe 33. The vacuum pipe supplies a maximum 2 kg/h water vapors and <1 kg/h dead air, so that the vacuum installation 35 has to suction off a maximum of 5 kg/h water vapor and 3 kg/h dead air at 1.33 mbar. The third burner stage, determined to be at 193.3 mbar and into which the waste gases from the degassing stage 4 and the preliminary stage 16 are also fed, is additionally charged with 2 kg/h water vapor and 2 kg/h dead air. With an entry temperature of 25° C. for the circulating water which is fed into the injection condenser of the vacuum installation, the water vapor part of the waste gas stream which has to be suctioned off by the vacuum installation 35 is already almost completely condensed, so that the subsequent stages are essentially only charged with the remaining inert gas. For the stated output the hourly use of steam from the necessary vacuum steam burner aggregate at 8 bar steam pressure is only 115.5 kg/h or 18.6 kg/to fatty acid distillate.

The distillate of 6232.4 kg/h which runs off from the main stage with a boiling temperature of 188° C. through the distillate pipe 36 is, as has already been mentioned, used in the counter current heat exchanger 11 for the initial heating the crude acid inflow from 60° C. to 140° C., the amount of heat being exchanged is 1,172,304 kJ/h. For a exchange surface of 50 m², the heat transfer number is k 136.9 kcal/m²·°C.·h. cooling of the distillate to 60° C. takes place in the subsequent distillate cooler 37, which is operated with cooling water with an entry temperature of 45° C. and an exit temperature of 60° C., and has a cooling surface of 60 m². The amount of heat to be removed is 753,624 kJ/h by the heat transfer number is k=119.5 kcal/m²·°C.·h.

The an acid stream of 460 kg/h is pumped with a circulation pump 30b of the falling film evaporator of the main stage 30 to the distributor 38b in the head 38a of the falling film evaporator pipe bundle 38c of the final stage 38 has a temperature of 212° C. The circulation portion of this falling film evaporator has a temperature of 238° C. at a pressure of 3.33 mbar in the corresponding separator 38d of 800 mm diameter. The circulation takes place through the suction and pressure pipes 38e by means of the circulation pump 38f. The pipe bundle 38c of the falling film evaporator 38 consists of 16 pipes with an outside diameter of 76 mm, a wall thickness of 2 mm, and a length of 2 m.

To avoid the formation of anhydrides, pure steam in the amount of 2 kg/h is fed into the falling film evaporator head 38a through the feed pipe 38g, which has at the same time the effect of lowering the boiling temperature correspondingly.

The amount of heat to be transferred in pipe bundle 38c is 113044 kJ/h. For the excahnge surface of 7.64 m² and a median temperature difference of 15° C., the corresponding heat transfer number is k=235.6 kcal/m²·°C.·h with a permissible pressure loss of 0.21 mbar and a circulation volume of 8 m³/h. pitch in the amount of 295 kg/h is drawn off through the pitch pipe 39, and then cooled in the pitch cooler from 238° C. 40 with an exchange surface of 4 m². Cooling the pitch heats the cooling water from 50° C. to 65° C. The amount of heat thus exchanged is 117230 kJ/h. Under these conditions, there is a heat exchange number k=96.6. Of the vapors rising in the separator room 38d of evaporator 38 with $V_L$=0.682 m/s only the 165 kg/h of fatty acid, but not the 2 kg/h of water vapor, are condensed in the condenser with the built-in gas cooling portion 38h which uses cooling water with an entry temperature of 50° C. and an exit temperature of 65° C. so as to remove 64895 kJ/h.

With an exchange surface, including gas cooling part, of 2.5 m², the median heat exchange number is 82.5 kcal/m²·°C.·h. The waste gas of 2 kg/h water vapor and <1 kg/h dead air leaving the condenser has a temperature of 60° C. For separating out liquid particles entrained in the waste gas, there is a small Euroform separator 30i directly above the condenser. If the resulting distillate is not fed into the preliminary column by the removal pump, it is removed through pipe 41 and the product cooler 42 having a cooling surface of 2.5 m² which cools the distillate from about 190° C. to 60° C. The amount of heat exchanged is 62216 kJ/h and the heat transfer number is k=82.5 kcal/m²·°C.·h.

I claim:

1. A process for degassing, dehydrating and separating percut during a straight-run distillation of crude fatty acids, said process comprising degassing the crude fatty acids in a first stage by effecting a counter current flow between the crude fatty acids and a stripping steam at a temperature below 100° C. and at a pressure between 67 and 400 mbar so as to avoid any appreciable dehydration or precut separation, feeding the degassed fatty acids to a dehydrating and precut separating second stage comprising a precut column having a stripping section with a distributor and a falling film dephlegmation section which is mounted above the distributor, the crude fatty acids being fed into the second stage near the distributor, heating the crude fatty acids in the second stage to form crude fatty acid vapors containing low boiling precut and water, partially condensing the vapors in the dephlegmation section to create reflux of fatty acids while the low boiling precut and water remain completely vaporized, withdrawing the vaporized low boiling point precut and water from the dephlegmation section, condensing the vaporized precut and water, and collecting the condensed precut and water in a decantation tank.

2. A process according to claim 1, wherein the degassing is conducted within the temperature range below 70° C. and with a working pressure between 133 and 267 mbar.

3. A process according to claim 2, wherein the degassing is conducted with 0.1-0.4 wt.% pure stripping steam, the steam being released into a bottom of the degassing stage as a stripping medium for stripping dissolved air and other inert gases from the crude fatty acids.

4. A process according to claim 3, wherein the second stage is conducted at a working pressure between 67 and 400 mbar.

5. A process according to claim 1, wherein stripping steam is fed into a bottom of the precut section.

6. A process according to claim 1, wherein the degassed crude fatty acids are preheated by passing through a cooling side of the falling film dephlegmation section, and thereafter are passed to the distributor of the stripper section.

7. A process according to claim 6, wherein the degassed crude fatty acid, prior to entering the second stage, is heated counter currently from 60° up to 140° C. by distillate from a main distillation stage being cooled down from 188° C. to 102° C., and, in a heat exchange condenser of the main stage, is further heated up to 175° C. and then, in the heat exchange with the cooling side of the falling film dephlegmation section is heated up to 180° C., and finally in another heat exchanger is brought up to a temperature of 225° C.

8. A process according to claim 5, further including feeding the fatty acids withdrawn from the second stage into a main stage, subjecting the fatty acids to evaporation in the main stage, withdrawing fatty acids from the main stage and feeding the acids to a final stage, subjecting the fatty acids to distillation in a falling film column in the final stage to yield distillate, feeding the distillate from the falling film column of the final stage into the liquid distributor for the stripping section of the second stage, so that degradation products which form in small amounts in the final stage and are dissolved in the distillate, are removed by the stripping steam before entry into the main stage.

* * * * *